United States Patent [19]
Cros

[11] Patent Number: 5,610,037
[45] Date of Patent: Mar. 11, 1997

[54] PRODUCTION OF POLYSACCHARIDES OF HIGH VISCOSITY USING XANTHOMONAS CAMPESTRIS AND GLYCOAMYLASE WITH FLUIDIZED STARCH

[75] Inventor: Patrick Cros, Melle, France

[73] Assignee: Rhone-Poulenc Chimie, Courbevoie Cedex, France

[21] Appl. No.: 379,111

[22] Filed: Jan. 27, 1995

Related U.S. Application Data

[63] Continuation of Ser. No. 914,000, Jul. 17, 1992, abandoned, which is a continuation of Ser. No. 675,945, Mar. 27, 1991, abandoned, which is a continuation of Ser. No. 279,653, Dec. 5, 1988, abandoned.

[30] Foreign Application Priority Data

Dec. 4, 1987 [FR] France .................................. 87 16855

[51] Int. Cl.$^6$ ....................................................... C12P 19/06
[52] U.S. Cl. ........................... 435/104; 435/101; 435/910
[58] Field of Search ................................... 435/101, 104, 435/910

[56] References Cited

U.S. PATENT DOCUMENTS

| | | | |
|---|---|---|---|
| 3,427,226 | 2/1969 | McNeely | 435/104 |
| 3,868,307 | 2/1995 | Van Lanen | 435/255 |
| 4,032,403 | 6/1977 | Sakai et al. | 435/99 |
| 4,075,405 | 2/1978 | Takahashi et al. | 435/101 |
| 4,104,123 | 8/1978 | Duc et al. | 195/31 P |
| 4,186,025 | 1/1980 | Kang et al. | 106/162 |
| 4,230,806 | 10/1980 | Nojiri et al. | 435/255 |
| 4,251,633 | 2/1981 | Orlowski et al. | 435/104 |
| 4,316,956 | 2/1982 | Lützen | 435/96 |
| 4,355,106 | 10/1982 | Lawford | 435/101 |
| 4,575,551 | 3/1986 | Fujiyama et al. | 536/123 |
| 4,775,632 | 10/1988 | Gozard et al. | 435/101 |
| 4,868,293 | 9/1989 | Vanderslice et al. | 536/123 |
| 5,175,278 | 12/1992 | Peik et al. | 536/123 |

FOREIGN PATENT DOCUMENTS

| | | |
|---|---|---|
| 0149915 | 7/1985 | European Pat. Off. . |
| 2165549 | 6/1986 | European Pat. Off. . |

OTHER PUBLICATIONS

Biotechnology, vol. 3 eds H. J. Rehm and G. Reed, Chapter 34, Sutherland IW, pp. 531–555 (1983).
Chemical Abstracts, May 09, 1988, vol. 108(19), P. 368, #164491k.
Chemical Abstracts, Dec. 18, 1972, vol. 77(25), p. 284, #163020k.
Chemical Abstracts, Oct. 26, 1987, vol. 107(17), p. 581, #152902m.

Primary Examiner—Irene Marx
Assistant Examiner—S. Saucier
Attorney, Agent, or Firm—Burns, Doane, Swecker & Mathis, L.L.P.

[57] ABSTRACT

Polysaccharide biopolymers, e.g., xanthan gum, are produced by the aerobic microbial fermentation of a carbohydrate in an aqueous nutrient medium containing starch as a source of carbon, and wherein the fermentation is carried out in the presence of a saccharide-specific amylolytic enzyme.

9 Claims, 1 Drawing Sheet

PRODUCTION OF POLYSACCHARIDES OF HIGH VISCOSITY USING XANTHOMONAS CAMPESTRIS AND GLYCOAMYLASE WITH FLUIDIZED STARCH

This application is a continuation of application Ser. No. 07/914,000, filed Jul. 17, 1992 now abandoned in turn, a continuation of Ser. No. 07/675,945, filed Mar. 27, 1991, now abandoned, in turn, a continuation of Ser. No. 07/279,653, filed Dec. 5, 1988, and now abandoned.

BACKGROUND OF THE INVENTION

1. Field of the Invention

The present invention relates to an improved process for the production of polysaccharides by the fermentation of carbohydrates utilizing microorganisms. More especially, this invention relates to a fermentation process using a starch or a hydrolysate of a starch as the source of nutritive carbon.

2. Description of the Prior Art

Fermentation polysaccharides having high molecular weights, or biopolymers, are increasingly in demand for numerous industrial applications by reason of their thickening, viscosifying and stabilizing properties in aqueous media. Thus, xanthan gum, in light of its exceptional rheological properties, is used in fields as varied as the building, paint, paper, textile, cosmetic and food industries, in agriculture, water treatment, drilling, petroleum recovery, and many others.

Biopolymers are products of aerobic cultures of microorganisms in an aqueous nutritive medium.

Xanthan gum is produced by bacteria of the species Xanthomonas. Biopolymers of the same type may be produced by a wide variety of microorganisms, including, among the best known, those of the species Agrobacterium, Arthrobacter, Alcaligenes (Succinoglycane), Pseudomona (Levan), Rhizobium, Sclerotium (Scleroglucane). These polysaccharides have high molecular weights, typically higher than $1 \times 10^6$ and consist of glucose, mannose, galactose, rhamnose, glucuronic acid, mannuronic acid, guluronic acid units, and possibly the acetate and pyruvate derivatives thereof. Their particular structures and properties are described, for example, in Whistler, *Industrial Gums*, 2nd Edition, Chapters XXI–XXIII (1973).

Numerous publications exist relating to the production of fermentation polysaccharides. Processes for the production of xanthan gum are described, for example, in U.S. Pat. Nos. 3,020,206, 3,251,749, 3,391,060, 3,271,267, 3,427,226, 3,433,708, 3,455,786, 3,485,719, 3,594,280, 4,154,654 and 4,282,321.

The nutrient medium normally contains, in addition to different growth elements, assimilable carbohydrates as the source of carbon. Suitable carbohydrates include glucose, saccharose, fructose, maltose, lactose, soluble starches and their hydrolysates. Although crude (raw) starch is described as a suitable source of carbon, it presents the major disadvantage of considerably extending the fermentation cycle relative to the monosaccharides, such as glucose. Furthermore, the microorganism is not capable of consuming all of the reducing sugars. The presence of these residual sugars at the end of the fermentation, on the one hand, renders the medium susceptible to the development of contaminating strains capable of degrading the wort prior to the separation of the polysaccharide. On the other hand, it may adversely color the product during the heat treatments of pasteurization and optional clarification.

SUMMARY OF THE INVENTION

Accordingly, a major object of the present invention is the provision of an improved and economical fermentation process for the production of polysaccharides using starch as the source of carbon and having a productivity at least equal to that realized using glucose or starch hydrolysates having a high glucose content.

Briefly, it has now unexpectedly and surprisingly been discovered that polysaccharides may be produced economically by carrying out the fermentation by means of a microorganism which simultaneously produces starch by enzymatic hydrolysis. The subject process surprisingly enables the production of a polysaccharide having improved rheological properties relative to those obtained from raw starch. Additional advantages ensue from a reduction of the duration of the fermentation, the elimination of residual dextrins of low molecular weight, and improved productivity.

The present invention features the production of polysaccharides by aerobic fermentation utilizing microorganisms, in an aqueous nutrient medium containing starch as the source of assimilable carbon, and wherein the fermentation is carried out in the added presence of at least one amylolytic saccharifying, or saccharide-specific enzyme.

DETAILED DESCRIPTION OF THE PREFERRED EMBODIMENTS OF THE INVENTION

Figure 1:
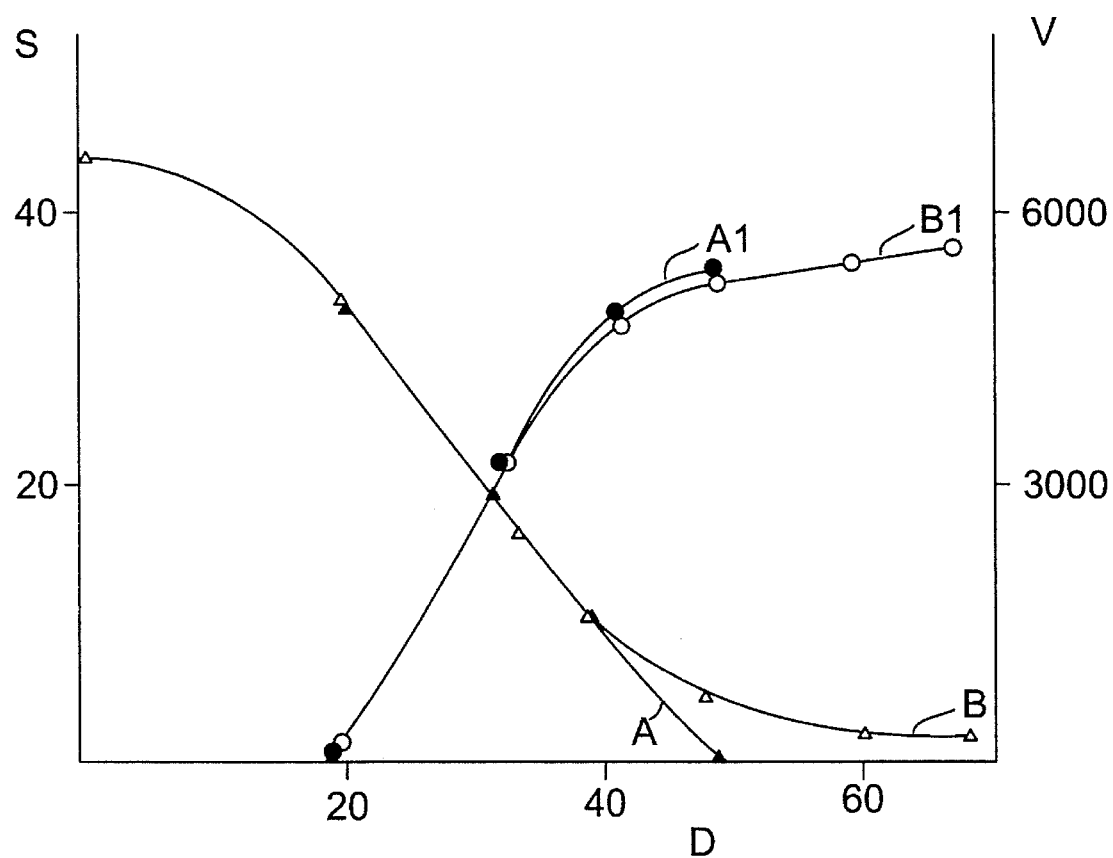

More particularly according to the present invention, the starch used as the carbon source may be any cereal starch, such as wheat starch, corn starch, sorghum, rice, tapioca, rye, oat starch, or the starch of a tuber, such as potato starch.

By the term "starch" as utilized herein are intended raw starch in an aqueous dispersion, and hydrolyzed starches resulting from the incomplete hydrolysis of starch, such as fluidized starch, starch syrups and hydrolysates rich in dextrose. Starch hydrolysates differ in their degree of hydrolysis, expressed as dextrose equivalents (D.E.) and their higher oligosaccharide and polysaccharide content. Fluidized starches have a D.E. of from approximately 3 to 20 and generally contain 50% to 95% polysaccharides with a degree of polymerization greater than G 7 (7 glucose units). The starch or glucose syrups with a low dextrose equivalent have a D.E. of from about 20 to 68, with 10% to 50% polysaccharides higher than G 7. Starch hydrolysates or syrups rich in dextrose have a D.E. of up to 90% to 98%. The preparation of hydrolyzed starches is well known to this art. Conventionally, fluidized starches and starch syrups are produced by acid and/or enzymatic hydrolysis by means of an liquefaction α-amylase, possibly followed by a β-amylase. For hydrolysates rich in glucose, the starch is usually converted in a two-stage process by the action of a liquefying α-amylase, followed by the action of a saccharifying enzyme, such as glucoamylase, also known as amyloglucosidase.

In practice, the process of the invention preferably employs a starch syrup and, even more preferably, a fluidized starch. The use of high glucose hydrolysates is not advantageous from an economic standpoint, as it requires prior saccharification, which is a lengthy stage, even under the conditions of maximum activity of amyloglucosidase, obtained at a temperature higher than 50° C. and a pH of 4.5 to 5.

Starch and its products of hydrolysis may be directly used in the process of the invention, in the nonpurified form after sterilization. Obviously, purified, concentrated or dehydrated commercial products, such as the maltodextrins, may also be used.

The starch is present in the fermentation medium in an amount necessary to supply 1% to 15% by weight glucose relative to the fermentation medium. Expressed as raw starch, on a dry basis, suitable amounts may range from 5 to 200 g/l, preferably from 10 to 150 g/l of the fermentation medium.

The amylolytic saccharifying enzymes added according to this invention to the fermentation medium containing the microorganism which produces a high molecular weight polysaccharide, are capable of converting the starch dextrins into glucose and maltose. Exemplary such saccharifying enzymes are the saccharifying α-amylases, such as the α-amylase of *Bacillus subtilis* var. *amylosaccharitens*, fungal α-amylase, the β-amylases, glucoamylase, isoamylase, pullulanase and the like. These enzymes may be used alone or as mixtures thereof.

Glucoamylase is preferred because of its high specificity. The glucoamylase may be all fungal glucoamylase, such as that belonging to the class Aspergillus, Endomyces or Rhizopus. In particular, in the case in which raw starch is used as the source of carbon, it is also possible to use a liquefying enzyme in addition to the saccharifying enzyme, for example a mixture of a liquefying α-amylase/β-amylase or a liquefying α-amylase/glucoamylase. Industrial enzymatic preparations are described in *Encycl. of Polymer Science*, vol. 6, pp. 46–53.

The amylolytic enzyme of saccharification, optionally of liquefaction, is added to the fermenting medium in an amount necessary to effect the saccharification and, respectively, the fluidizing of the starch. The minimum amount used is a function of the activity of the enzyme and the quantity of the D.E. of the starch present in the medium, and may be easily determined by one skilled in this art. In general, amounts sufficient to yield 0.02 to 4 units of enzymatic activity, preferably 0.1 to 2 units, per gram of starch (expressed as dry solids). As an example of a saccharifying enzyme, AMG 200 D®, marketed by NOVO INDUSTRY is illustrative; it is a glucoamylase and may be added in an amount of 0.01 to 2%, preferably from 0.05% to 1% by weight, based on the weight of the solids contained in the liquefied starch present in the fermenting medium.

The process of the invention is useful for the production of all exocellular polysaccharides by the fermentation of glucides by means of microorganisms. Numerous microorganisms, such as bacteria, yeasts, fungi, algae, are capable of producing exocellular polysaccharides. Exemplary thereof, the following are representative:

(i) bacteria belonging to the species Xanthomonas and more particularly the strains described in Bergey's *Manual of Determinative Bacteriology* (8th Ed., 1974, Williams N. Wilkins Co., Baltimore), such as *Xanthomonas begoniae, Xanthomonas campestris, Xanthomonas carotae, Xanthomonas hederae, Xanthomonas incanae, Xanthomonas malvacearum, Xanthomonas Papavericola, Xanthomonas phaseoli, Xanthomonas pisi Xanthomonas vasculorum, Xanthomonas vesicatoria, Xanthomonas vitians, Xanthomonas pelargonii*; bacteria of the species Arthrobacter and more particularly the strains *Arthrobacter stabilis, Arthrobacter viscosus*; the species Erwinia; the species Azotobacter and more particularly the strain *Azotobacter indicus*; the species Agrobacterium and more particularly the strain *Agrobacterium radiobacter, Agrobacterium rhozigenes, Agrobacterium tumefaciens*; the species Alcaligenes and more particularly *Alcaligenes faecalis*; the species Pseudomonas and more particular *Pseudomonas methanica*: the species Corynebacterium; the species Bacillus and more particularly *Bacillus polymyxa*;

(ii) fungi belonging to the species Sclerotium and more particularly the strains *Sclerotium glucanica, Sclerotium rolfsii* or *Plectania occidentalis*; and (iii) yeasts belonging to the species Hansenula such as the strain *Hansenula capsulata*.

In addition to the carbon source and the amylolytic enzyme used according to the invention, the fermentation medium and the fermentation conditions may be selected from among those described in the literature for each of the microorganisms. Appropriate fermentation media are described, for example, in Sydney J. Gutcho, *Chemicals by Fermantation*, Noyes Data Corp. (1973).

A typical aqueous fermentation medium comprises, in addition to the source of carbon, a source of organic and/or inorganic nitrogen, such as the soluble extract of corn (CSL) and/or soy beans, a yeast extract, peptones, gelatin, casein, ammonium salts, such as ammonium chloride, ammonium nitrate, ammonium carbonates, ammonium sulfates, nitrates, such as sodium or potassium nitrates. The fermentation medium may further contain a source of assimilable phosphorus, which is introduced initially or during the adjustment of the pH during fermentation, for example over the course of fermentation in the form of $PO_4^-$ ions, together with a source of magnesium, such as magnesium sulfate, magnesium acetate, magnesium chloride, magnesium nitrate, and traces of oligoelements essential for growth and multiplication, the nature of which depends on the strain of microorganism used.

Concerning the practicalities of carrying out the process of this invention, these are described in the existing literature. See particularly the processes described in the patents noted above relative to the preparation of the xanthan gum. In most cases, the details of the production of polysaccharides by means of the other microorganisms mentioned above are very close to those of xanthan gum.

In general, the microorganism is introduced into the fermentation medium in known fashion, for example by means of intermediate cultures obtained in 20 liter laboratory fermentors, which themselves are obtained from inoculums prepared, for example, in a 1 liter Erlenmeyer flask.

The preparation of the inoculums or intermediate cultures is well known to this art and is described, for example, in FR 2,414,555.

The fermentation is then carried out for several days in the aerated and agitated medium in one or more growth and production stages. The growth and production media may have the same or different compositions. The incubation temperature and the time required to generate an acceptable percentage of polysaccharide naturally vary with the microorganism used. The temperature generally is approximately 30° C.±10° C. In most cases, the pH is maintained within a range of 6 to 7.5 and preferably from 6.5 to 7.2. It is possible to use a pH regulating system which introduces into the medium, if necessary, an alkaline reagent, such as sodium or potassium hydroxide, or ammonia. However, in certain cases the optimum may be in a lower pH range. For example, in the production of scleroglucane the yield is optimum in an initial pH range of 3.5 to 5.5 (FR 1,386,287).

In order to obtain rapid fermentation, it is essential that the medium be adequately aerated and agitated to yield the correct amount of oxygen available to the bacterial culture that is being grown. The oxygen requirements of the fermentation are adjusted in conventional manner to the fermentation and oxygen transfer conditions. In this regard, it is noted that the process of the invention may be adapted to processes of fermentation in an emulsified medium, as described in EP-A-58,364, EP-A-98,474 and EP-A187,092.

After fermentation has been achieved, the wort containing the polysaccharide is treated in a manner known in and of itself. Generally, pasteurization is carried out to kill the microbial cells. If so desired, the wort may be subjected to heat and/or enzymatic treatments and/or filtration to improve rheological properties, for clarification and for filterability. It may also be advantageous in certain cases to concentrate the wort, which may be carried out by any conventional means.

The polysaccharide may be isolated from the wort by any known method, such as precipitation by means of a solvent in which the product is insoluble, for example a lower alcohol, preferably isopropanol and/or a suitable inorganic salt. The polysaccharide prepared is then filtered, washed, dried and ground.

The process described above may obviously be carried out discontinuously, or continuously by the continuous introduction of a sterile medium into the fermentation vessel.

It will be appreciated that the above description relates to a specific process for the preparation of biopolymers by fermentation by means of a medium containing a source of carbohydrate produced from starch, in the presence of enzymes capable of hydrolyzing the starch or its degradation products into mono- or disaccharides and that the invention itself is not limited to specified compounds of the fermentation medium nor to any particular mode of embodiment.

The entire culture medium and the polysaccharide powders may be used for any known applications of the hydrocolloids. The aqueous solutions obtained by the dilution of the wort or the solubilization of the powder have been found to have rheological properties higher than those obtained by the dilution, in the same concentrations, of a polysaccharide produced from raw starch or liquefied starch, by the processes of the prior art.

In order to further illustrate the present invention and the advantages thereof, the following specific examples are given, it being understood that same are intended only as illustrative and in nowise limitative.

EXAMPLE 1

Preparation of the Inoculum

Into the culture of Xanthomonas campestris maintained on agar-agar in a test tube, in an agitated flask, 100 ml of a medium containing a yeast extract, malt extract, bactopeptone and 10 g/l wheat starch were introduced. The modified medium was incubated after sterilization for 24 hours at 28° C. The contents of the flask were used to inoculate 15 l of the fermentation medium.

Preparation of fluidized raw starch

A milk of wheat starch containing 30% by weight of dry solids was prepared. The pH was adjusted to 7 and a fluidizing enzyme (TERMANYL 120 D®—NOVO Industry) was added in a proportion of 0.15% by weight relative to the starch, expressed as the solids thereof. The temperature was increased to 85° C. and maintained at this value for 30 min. The fluidized starch was sterilized at 30 min at 121° C.

Fermentation

Experiment A

In a 20 l fermentor, 15 l of sterile production medium having the following composition were prepared:

| (i) Starch (prepared as above) | 45 g/l (dry solids) |
| (ii) Soy bean flour | 5.1 g/l |
| (iii) $MgSO_4.7H_2O$ | 0.25 g/l |
| (iv) Distilled water | q.s.p. 1 liter |
| (v) pH adjusted to 7 | |

A glucoamylase was added (AMG 200 D®—NOVO Industry) in a proportion to 1% relative to the starch, expressed as dry solids thereof.

Immediately following the addition of the enzyme, the medium was inoculated with an inoculum prepared as above.

The temperature was controlled at 28° C. and the pH maintained at 6.8 to 7.0 by the automatic addition of sodium hydroxide. Air was injected into the fermentor with an initial aeration of 40 VVH, increased to 55 VVH when the viscosity of the medium began to increase. The medium was agitated by 3 stages by Rushton blades at a velocity of 200 to 400 rpm.

The fermentation was discontinued when no sugars remained. The wort was pasteurized and then the polysaccharide was precipitated by the addition of isopropanol, filtered and dried at 30 min at 120° C.

Experiment B (Comparative)

The operating conditions were identical with those of Experiment A, except that no glucoamylase was added to the production medium. Fermentation was discontinued when the concentration in residual sugar no longer changed.

Over the course of Experiments A and B, samples of the wort were taken at regular intervals to measure the amount of residual starch in the medium. The measurement was carried out by high performance liquid chromatography after the acid hydrolysis of the starch. The viscosity of the medium (Brookfield viscosimeter, needle No. 4, 30 rpm, 20° C.) was also measured. The results are shown graphically in FIG. 1, wherein the curves A, A1 and B, B1 represent the amount of residual starch (S) in g/l and the viscosity of the medium (V) in mPa.s as a function of the duration (D) in hours of the fermentation of Experiments A and B, respectively. The fermentation results were:

|  | Experiment A | Experiment B |
| --- | --- | --- |
| Duration of fermentation | 50 h | >66 h |
| Final residual sugars | 0 | >2 g/l |
| Precipitable dry solids | 31.3 g/kg | 29.2 g/kg |
| Raw starch yield | 69.6% | 64.9% |

The viscosifying power of the products was measured in each case on dilute aqueous solutions prepared from powder at a concentration of 0.2% in distilled water (Brookfield—Needle No. 1, 20° C.). The results were as follows:

|  | Experiment A | Experiment B |
| --- | --- | --- |
| 6 t/min | 600 mPa.s | 350 mPa.s |
| 30 t/min | 190 mPa.s | 135 mPa.s |

EXAMPLES 2 AND 3

Two fermentations were carried out in the manner described in Example 1, using the same media and operating conditions. Following the establishment of the production medium, 0.25% (Example 2) or 0.5% (Example 3) of the enzyme AMG 200 D®/starch as the dry solids were added.

The results were as follows:

|  | Example 2 | Example 3 |
| --- | --- | --- |
| Precipitable dry solids | 30 g/kg | 29.7 g/kg |
| Duration of fermentation | 66 h | 50 h |
| Yield/raw starch | 66.7% | 66% |
| Viscosity (mPa.s) 0.2% sol |  |  |
| 6 t/min | 375 | 575 |
| 30 t/min | 150 | 192 |

EXAMPLE 4

The fermentation was carried out in the manner described in Example 1, with an identical inoculation and a fluidized starch prepared under the same conditions.

The production medium had the following composition:

| (i) Fluidized starch | 100 g/l |
| --- | --- |
| (ii) Raw soy bean flour | 7.0 g/l |
| (iii) MgSO$_4$.7H$_2$O | 0.25 g/l |
| (iv) Distilled water | q.s.p. |

After establishing the production medium, and prior to the inoculation, 0.5% glucoamylase AMG 200 D® relative to the weight of the starch, expressed as dry solids, was added. The fermentation conditions were identical with those of Example 1.

The following results were obtained, compared with an experiment carried out under identical conditions, but in the absence of glucoamylase.

|  | Example 4 | Comparative |
| --- | --- | --- |
| Precipitable dry solids | 54 g/kg | 49.5 g/kg |
| Duration of fermentation | 130 h | >160 h |
| Residual sugars after fermentation | 0 | >15 g/l |
| Yield/starch | 54 | 49.5 |

As the comparative experiment was not extractable in view of the high residual sugar content, the viscosifying power was not measured.

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A fermentation process for the production of polysaccharides comprising:

(i) culturing *Xanthomonas campestris* in a fermentation medium comprising a fluidized starch having a dextrose equivalent ranging from about 3 to 20 and containing about 50% to 95% polysaccharides with a degree of polymerization greater than 7 glucose units and glucoamylase under conditions which result in the formation of polysaccharides having increased viscosity; and (ii) recovering said polysaccharides of increased viscosity from the fermentation medium, wherein said *Xanthomonas campestris* is capable of assimilating said fluidized starch in the absence of said glucoamylase and wherein the addition of said glucoamylase results in the formation of said polysaccharides having increased viscosity relative to an otherwise identical fermentation process effected in the absence of said glucoamylase.

2. The process as defined by claim 1, wherein the amount of starch is such as to provide 1% to 15% calculated by weight of glucose relative to the weight of the fermentation medium.

3. The process as defined by claim 2, wherein the fermentation medium comprises from 5 to 200 g/l of starch.

4. The process as defined by claim 3, wherein the fermentation medium comprises from 10 to 150 g/l of starch.

5. The process as defined by claim 1, wherein the glucoamylase is present in such amount as to provide 0.02 to 4 units of enzymatic activity per gram of starch, expressed as the dry solids content thereof.

6. The process as defined by claim 5, wherein the glucoamylase is present in such amount as to provide 0.1 to 2 units of enzymatic activity per gram of starch.

7. The process as defined by claim 1, wherein the amount of said glucoamylase ranges from 0.01% to 2% by weight of the starch expressed as the dry solids content thereof.

8. The process as defined by claim 7, wherein the amount of said glucoamylase ranges from 0.05% to 1% by weight of the amount by weight of the starch.

9. The fermentation process of claim 1, wherein said process is conducted at a temperature of approximately 30° C. ±10° C. and at a pH ranging from about 6 to about 7.5.

* * * * *